United States Patent [19]

Armstrong

[11] Patent Number: 5,496,832
[45] Date of Patent: Mar. 5, 1996

[54] METHOD OF TREATING CARDIAC INFLAMMATORY DISEASE

[75] Inventor: Jay J. Armstrong, Bensalem, Pa.

[73] Assignee: American Home Products Corporation, Madison, N.J.

[21] Appl. No.: 401,747

[22] Filed: Mar. 9, 1995

[51] Int. Cl.$^6$ .................................................. A61K 31/44
[52] U.S. Cl. .................................................. 514/291
[58] Field of Search ............................................. 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,401,653 | 8/1983 | Eng | 514/291 |
| 4,885,171 | 12/1989 | Surendra et al. | 514/291 |
| 5,078,999 | 1/1992 | Warner et al. | 514/291 |
| 5,080,899 | 1/1992 | Sturm et al. | 514/291 |
| 5,100,899 | 3/1992 | Calne | 514/291 |
| 5,206,018 | 4/1993 | Sehgal et al. | 514/291 |
| 5,286,730 | 2/1994 | Caufield et al. | 514/291 |
| 5,286,731 | 2/1994 | Caufield et al. | 514/291 |
| 5,288,711 | 2/1994 | Mitchell et al. | 514/291 |
| 5,321,009 | 6/1994 | Baeder et al. | 514/291 |
| 5,387,589 | 2/1995 | Kulkarni | 514/291 |

FOREIGN PATENT DOCUMENTS

| | | | |
|---|---|---|---|
| 507555A1 | 7/1992 | European Pat. Off. | 514/291 |

OTHER PUBLICATIONS

Chandrasoma, P., Concise Pathology, Appleton and Lange 1:398–400 (1991).

Rubin, E., et al., Pathology, J. B. Lippincott Company 402–413, 434, & 527–539 (1988).

Andreoli, T., Essentials of Medicine, W. B. Saunders, Pub., 349–360 (1986).

Cabeza Meckert, P. M. et al., Clin. Immunology and Immunopathology, 60:137 (1991).

Gea, S., et al., American Journal of Trop. Med. Hyg. 49(5):581–588 (1993).

Venzina, C., J. Antibiot. 28:721 (1975).

Sehgal, S. N., J. Antibiot. 28:727 (1975).

Baker, H. J., Antibiot. 31:539 (1978).

Martel, R. R., Can. J. Physiol. Pharmacol. 55:48 (1977).

Staruch, M. J., FASEB 3:3411 (1989).

Dumont, F. J., FASEB 3:5256 (1989).

Calne, R. Y., Lancet 1183 (1978).

Morris, R. E., Med. Sci. Res. 17:877 (1989).

Baeder, W. L., Fifth Int. Conf. Inflamm. Res. Assoc. 121 (Abstract) (1990).

Meiser, B. M., J. Heart Lung Transplant. 11 (pt. 2):197 (1992).

Stepkowski, S. M., Transplantation Proc. 23:507 (1991).

*Primary Examiner*—Jerome D. Goldberg
*Attorney, Agent, or Firm*—Arnold S. Milowsky

[57] ABSTRACT

This invention provides a method of treating cardiac inflammatory disease which comprises administering rapamycin to said mammal orally, parenterally, intravascularly, intranasally, intrabronchially, transdermally, or rectally.

2 Claims, No Drawings

METHOD OF TREATING CARDIAC INFLAMMATORY DISEASE

BACKGROUND OF THE INVENTION

Myocarditis and cardiomyopathy are a group of diseases primarily of the myocardium that are not the result of hypertensive, congenital, ischemic, or valvular heart disease. Myocarditis generally defines acute myocardial disease characterized by inflammation, and cardiomyopathy defines more chronic myocardial diseases in which the inflammatory features am not conspicuous. [Concise Pathology, 1st ed., Appleton & Lange, 367 (1991)]. Cardiomyopathies can be classified according to pathophysiologic type as dilated congestive, hypertrophic obstructive, hypertrophic non obstructive, apical obliterative, diffuse nonobliterative restrictive, and obliterative restrictive. Myocarditis and cardiomyopathy can lead to fever, chest pain, leukocytosis, increased erythrocyte sedimentation rate, left ventricular failure, arrythmias, heart block, ECG changes, and eventually cardiac failure.

Myocarditis and cardiomyopathy result from an immune response against the myocardium, including lymphocytic infiltration and inflammation. The immune response can occur secondary to infectious diseases such as Chagas' disease (American trypanosomiasis), toxoplasmosis, trichinosis, ricksettal infection (typhus, Rocky Mountain spotted fever), fungal infections, and metazoan parasites; or secondary to autoimmune diseases such as rheumatic fever, rheumatoid arthritis, systemic lupus erythematosus, progressive systemic sclerosis, and polyarthrits nodosa. The immune response leading to myocarditis can be idiopathic in nature as seen in Fiedler's myocarditis. Additionally, myocarditis can be caused by drug reaction to penicillin or sulfonamide, for example.

Acute endocarditis is defined as an inflammatory disease of the visceral or parietal pericardium [Pathology, J. B. Lippencott Co, 538 (1988)], and can occur secondary to bacterial, vital (especially echovirus, and Coxsackie Group B), or fungal infection, and can accompany systemic diseases such as rheumatoid arthritis, systemic lupus erythematosus, scleroderma, and uremia. [Merck Manual, 15th Ed. 537–8 (1987)]. Pericarditis can also occur after cardiac trauma or cardiac surgery that is suggested as being caused by immunologic hypersensitivity. Acute pericarditis can lead to chronic constrictive pericarditis, effusion, and hemorrhage, all of which can result in cardiac failure.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080, 899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

DESCRIPTION OF THE INVENTION

This invention provides a method of treating cardiac inflammatory disease in a mammal in need thereof which comprises administering an effective amount of rapamycin to said mammal orally, parenterally, intravascularly, intranasally, intrabronchially, transdermally, or rectally. In particular, this invention is useful in treating myocarditis, cardiomyopathy, endocarditis, and pericarditis which are at least in part attributed to an alloimmune or autoimmune condition or disease. More particularly, this invention is useful in treating myocarditis and cardiomyopathy resulting from infectious diseases such as Chagas' disease (American trypanosomiasis), toxoplasmosis, trichinosis, rickserial infection (typhus, Rocky Mountain spotted fever), fungal infections, and metazoan parasites, autoimmune diseases such as rheumatoid fever, rheumatoid arthritis, systemic lupus erythematosus, progressive systemic sclerosis, and polyarthrits nodosa, that are idiopathic in nature, such as Fiedler's disease, or resulting from drug reaction to penicillin or sulfonamide, for example; endocarditis resulting from bacterial, viral (especially echovirus, and Coxsackie Group B), fungai infection, or systemic diseases such as rheumatoid arthritis, systemic lupus erythematosus, scleroderma, and uremia; and pericarditis occurring after cardiac trauma or cardiac surgery.

Treating covers treatment of an existing condition, inhibiting the progress or development of the condition, ameliorating the condition, and providing palliation of the condition.

The effect of rapamycin on cardiac inflammatory disease was established in an in vivo standard pharmacological test procedure that emulates immune mediated myocarditis in humans.

Briefly, male Lewis rats 300–350 g, were weighed and sedated with an i.p. injection of 20 mg of pentobarbital prior to baseline ECG recording. The rats were divided into four groups. The rats in Group 1 served as a control group for rats developing myocarditis, and received cardiac myosin only as described below. The rats in Group 2 served as a control group for rapamycin and received rapamycin only as described below. The rats in Groups 3 and 4 were immunized with cardiac myosin and then treated with rapamycin as described below.

The rats in Groups 1, 3 and 4, received a subcutaneous injection in the left rear foot pad of 100 μg of porcine cardiac myosin, suspended in 0.1M phosphate buffered saline. Seven days later, the rats in Groups 1, 3, and 4 were re-immunized with the same myosin concentration in the contralateral foot pad. Intraperitoneal administration of rapamycin was initiated on the first day of immunization at 1 mg/kg/day (Group 3; n=10), and 12 mg/kg/day (Group 4; n=6), using vehicle (20% dimethyl acetamide, 10% Tween 80, and 70% polyethylene glycol) and was maintained daily for fourteen days. The rats in Group 1 (n=10), received an i.p. injection of vehicle alone daily for fourteen days. The rats in Group 2 (n=7) were not immunized, but received a fourteen day daily i.p. regimen of rapamycin at 1 mg/kg/day. The treatment regimens are summarized in the table below.

| Group | n | Porcine Cardiac Myosin | Rapamycin |
|---|---|---|---|
| 1 | 10 | immunization on days 1 and 7 | — |
| 2 | 7 | — | 1 mg/kg/day days 1–14 |
| 3 | 10 | immunization on days 1 and 7 | 1 mg/kg/day days 1–14 |
| 4 | 6 | immunization on days 1 and 7 | 12 mg/kg/day days 1–14 |

TREATMENT REGIMENS

All animals were evaluated daily for lethargy, pallor or other obvious deficits, and ECGs were obtained on day 7, 14, 21 and 28.

ECGs were obtained according to the following procedure. All animals were shaved in the area of the ventral cervical thorax, the right dorsal pelvic girdle and the ventral pelvic girdle. They were identically marked at the four standard ECG limb electrode sites (right and left fore limbs, right and left hind limbs), and the standard dorsal posterior ground electrode site with a tattoo marker; and, using a recorder with a chart speed of 100 mm/sec, a baseline day 0 lead II ECG was obtained. The tattoo marks served as permanent reference points for future recording. Electrocardiographic profiles were obtained on days 7, 14, 21 and 28. In each instance, they were compared to the individuals' baseline ECG and to the corresponding day ECG of Group 2. Initial and terminal heart rates were determined, and the mean values in millimeters, of the following standard ECG variables were obtained by caliper measurement of four different cardiac complexes per individual record.

1)—ORS complex length (msec)
2)—$Q_\alpha T$ segment length (msec)
3)—R—R segment length (msec)
4)—Heart Rate (beats/min)

On day 28, all surviving animals were anesthetized with an i.p. injection of 20 mg pentobarbital, weighed, and final ECGs were obtained. They were then euthanized by excess $CO_2$ inhalation, and the heart, spleen, right kidney and liver were inspected, removed, weighed and placed in sterile containers, containing 25 ml of 10% buffered formalin. Terminal heart weights were recorded as both individual values and as a ratio of heart to terminal body weight for all groups. Macroscopic evaluation of organs was achieved through application of the following gross pathology scoring system:

0)—no obvious hypertrophy or lesions.
1)—the presence of hypertrophy and/or a single well defined lesion.
2)—the presence of hypertrophy and multiple lesions.

The hearts were removed from the formalin and a transversal cut was made immediately below the atrioventricular groove; the ventricles were then embedded in paraffin, for sectioning and staining. A microtome was used to cut 5 μm thick sections which were immediately stained with hematoxylin and eosin, and examined with a microscope at 100× and 400× magnification. Approximately seven sections per ventricle were evaluated to ensure uniformity and to determine a mean histopathologic score for individual animals of both control and experimental groups. There were no discernible differences among these sections for any individual animal examined. Photomicrographs were obtained. Microscopic evaluation of cardiac tissue was achieved through application of the following system:

0)—no lymphocytic infiltration visible throughout myocardium.
1)—moderate infiltration within an area not exceeding 0.25 mm².
2)—moderate or multiple infiltration within an area <4.0 mm².
3)—multiple infiltrates within an area >4.0 mm².

The results obtained in the standard pharmacological test procedure demonstrate that rapamycin is useful in treating cardiac inflammatory disease; these results are summarized below.

Frankly abnormal changes were observed in all animals in Group 1 (cardiac myosin only) in the listed ECG parameters compared with individual day 0 and day 28 records or compared with the rats in Group 2 (nonimmunized naive rats receiving rapamycin). The QRS, $Q_\alpha T$, R—R length complexes and heart rates displayed significant (p<0.01), mean variation from baseline values (changes: −32.6%, −17%, +19.6% and −14.3% respectively) for the rats in Group 1. Analysis of percent baseline changes of ECG complex values for the rats in Group 1, were statistically significant, compared with both the initial values and rapamycin treated groups (p<0.01). Significant pathologic differences were clearly visible in all comparisons of day 0 and day 28 lead II ECGs in animals from this group.

In no case did any cardiac myosin immunized, rapamycin treated animals (Groups 3, or 4) display significant changes in the listed ECG parameters compared with individual day 0 and day 28 records or compared with the rats in Group 2 (nonimmunized naive rats receiving rapamycin). The QRS, $Q_\alpha T$, R—R length complexes and heart rates demonstrated no significant mean variation (p>0.01), from baseline values (Group 3 changes: +5.2%, +4.8%, +4.6% and −1.7% respectively; Group changes: −0.27%, +6.7%, −2.8% and +0.09% respectively). No significant pathologic differences can be determined in comparisons of day 0 and day 28 lead II ECGs in any animals from Group 3.

According to the procedure described above, the animals were weighed, and the hearts were examined for gross pathological changes. The results are summarized in the table below.

| | MEAN GROSS PATHOLOGICAL RESULTS | | | | |
|---|---|---|---|---|---|
| Treatment Group* | Initial Body Wt. (grams) | Final Body Wt. (grams) | Heart Wt. (grams) | Heart/Body Wt. Ratio | Cardiac Pathology Score |
| 1 | 333.0 | 309.8 | 1.74 | 0.0056 | 1.8 |
| 2 | 331.3 | 361.3 | 0.93 | 0.0026 | 0.0 |
| 3 | 338.7 | 314.6 | 0.90 | 0.0029 | 0.0 |
| 4 | 326.7 | 267.5 | 0.85 | 0.0032 | 0.0 |

*Group 1 - cardiac myosin only; Group 2 - rapamycin 1 mg/kg/day; Group 3 - cardiac myosin immunization, and rapamycin 1 mg/kg/day; Group 4 cardiac myosin immunization, and rapamycin 12 mg/kg/day.

In all animals of Group 1, extensive heart and liver hypertrophy, accompanied by slight to moderate splenomegaly and a fulminating vasculitis of the great cardiac vessels (which may be attributable to local hypertension), was noted. The rated system of gross pathology for the control organ group was significantly different from that of Group 2 organs ($p<0.001$). The cardiac pathology of the rats of Group 1 was severely expressed, with multiple, well defined 1–4 mm lesions throughout the ventricular compartments (mean macroscopic score=1.8). Significant increases ($p<0.01$), in the terminal heart weights, heart to body weight ratio and gross enlargement of the spleen were also consistently observed for the rats of Group 1. Moreover, this group exhibited markedly lethargic behavior, stimulus unresponsiveness and ruffled fur from day 21 onward.

In no case did any rapamycin treated group demonstrate gross cardiac, liver, kidney or spleen pathology ($p<0.01$; mean macroscopic score=0). In addition, the terminal heart weights, heart to body weight ratios and spleen weights were well within comparable statistical limits ($p<0.01$), with the Group 2 rats. Treatment groups 3 and 4 presented no overt changes in appearance or activity throughout the duration of the test procedure.

The histopathologic results that were obtained are summarized as follows. In all animals of Group 1, multiple zones of lymphocytic infiltration, with fibrotic substitution and recruitment in cardiocyte depleted zones were noted (mean microscopic score=2.8). All comparisons of histopathologic differences of the rats of Group 1 versus Groups 3 and 4 were significant ($p<0.001$). In several cases, the fibrotic plaques were transmural and involved an entire ventricular hemisphere. Additionally, the tunica media and intima of the coronary arterioles in Group 1 were frequently ablated and numerous adherent lymphocytes were apparent around the vascular lumen.

In no case did any rapamycin treated group display remarkable microscopic pathology (mean microscopic score=0). The epicardium and myocardium of Groups 3 and 4 was contiguous, intact and well defined with robust cardiocytes and no lymphocytic infiltration or fibrotic deposition. Histopathologic comparison of Groups 3 and 4 was not statistically significant ($p>0.001$). Moreover, the tunica media and intima of the coronary arterioles is distinct, contiguous with the myocardium, and devoid of lymphocytic infiltrate or fibrotic substitution.

These results demonstrate that rapamycin inhibited the formation of immune mediated myocarditis in a standard pharmacological test procedure that emulates cardiac inflammatory disease in humans. Based on these results, rapamycin is useful in treating cardiac inflammatory disease, and is particularly useful in treating myocarditis, cardiomyopathy, endocarditis, and pericarditis which are at least in part attributed to an alloimmune or autoimmune condition or disease.

Rapamycin can be formulated neat or with a pharmaceutical carrier to a mammal in need thereof. The pharmaceutical carrier may be solid or liquid. When formulated orally, it has been found that 0.01% Tween 80 in PHOSAL PC-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. Rapamycin can also be administered orally either in liquid or solid composition form.

Rapamycin may be administered rectally in the form of a conventional suppository. For administration by intranasal or intrabronchial inhalation or insufflation, rapamycin may be formulated into an aqueous or partially aqueous solution, which can then be utilized in the form of an aerosol. Rapamycin may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, rapamycin may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected intravenous daily dosages of active compound would be 0.1 µg/kg–100 mg/kg, preferably between 0.001–25 mg/kg, and more preferably between 0.01–5 mg/kg. Projected daily oral dosages of rapamycin would be 0.005–50 mg/kg, preferably between 0.01–25 mg/kg, and more preferably between 0.05–10 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A method of treating myocarditis, cardiomyopathy, endocarditis, and pericarditis in a mammal in need thereof which comprises administering an effective amount of rapamycin to said mammal orally, parenterally, intravascularly, intranasally, intrabronchially, transdermally, or rectally.

2. The method according to claim 1, wherein the route of administration is oral or parenteral.

* * * * *